United States Patent [19]

Kojima et al.

[11] Patent Number: 5,391,527
[45] Date of Patent: * Feb. 21, 1995

[54] REGENERATION OF A MODIFIED ALKYLATION CATALYST WITH HYDROGEN

[75] Inventors: Masami Kojima, Mt. Prospect; Joseph A. Kocal, Gurnee, both of Ill.

[73] Assignee: UOP, Des Plaines, Ill.

[*] Notice: The portion of the term of this patent subsequent to May 10, 2014 has been disclaimed.

[21] Appl. No.: 172,960

[22] Filed: Dec. 27, 1993

Related U.S. Application Data

[63] Continuation-in-part of Ser. No. 43,954, Apr. 5, 1993, Pat. No. 5,310,713.

[51] Int. Cl.$^6$ .................. B01J 23/96; B01J 27/32; B01J 38/10; B01J 38/58
[52] U.S. Cl. .................. 502/53; 502/30; 502/31; 502/32; 502/35; 585/721
[58] Field of Search .................. 502/53, 30, 31, 32, 502/35; 585/721

[56] References Cited

U.S. PATENT DOCUMENTS

| | | | |
|---|---|---|---|
| 2,999,074 | 9/1961 | Block et al. | 502/227 |
| 3,318,820 | 5/1967 | Muller et al. | 502/35 |
| 3,352,941 | 11/1967 | Shoen et al. | 502/53 |
| 3,893,942 | 7/1975 | Yang | 502/53 |
| 4,098,833 | 7/1978 | Wristers | 260/666 |
| 5,310,713 | 5/1994 | Kojima et al. | 502/30 |

*Primary Examiner*—Paul E. Konopka
*Attorney, Agent, or Firm*—Thomas K. McBride; Eugene I. Snyder

[57] ABSTRACT

Catalytic composites of the reaction product of a metal halide having Friedel-Crafts activity with the bound surface hydroxyl group of inorganic oxides and containing a zerovalent metal with hydrogenation activity, often are effective catalysts in motor fuel alkylation which, however, undergo rapid deactivation. Deactivated catalysts are readily regenerable by treating the composite from which alkylate feedstock has been removed with hydrogen at temperatures in the range of 10° to 300° C. Multiple regenerations are possible without appreciable activity loss.

17 Claims, No Drawings

REGENERATION OF A MODIFIED ALKYLATION CATALYST WITH HYDROGEN

CROSS REFERENCE TO RELATED APPLICATION

This application is a continuation-in-part of U.S. Pat. application Ser. No. 08/043,954, filed Apr. 5, 1993, now U.S. Pat. No. 5,310,713, all of which is hereby incorporated by reference.

BACKGROUND OF THE INVENTION

Even in the era of anti-knock additives such as tetraethyl lead, the use of alkylate as a component in motor fuel gained both universal acceptance and importance. In the ensuing years alkylate has become an even more important component of motor fuel. Alkylate is an economical, clean-burning, high-octane, low volatility product that is becoming increasingly important as the composition of gasoline changes in response to environmental concerns and legislation. The governmental regulations most applicable to the increasing importance of alkylates are those affecting lead and butane. Adding lead anti-knock compounds was the easiest way to raise gasoline octane, but because of continuing concerns over the effects of lead emissions the phasing out of lead in gasoline was required, a process over 90% complete. Butane is another effective octane-booster but tends to evaporate from gasoline, especially in warm weather, contributing to smog formation. Recent EPA regulations have effected their virtually complete removal from gasoline.

The term "alkylate" generally refers to a complex mixture resulting from the alkylation of olefins present or formed in a feedstream of C2–C6 olefins with intermediates arising primarily from alkanes, especially branched alkanes, and predominantly those with 4 carbon atoms, especially isobutane, also present in the same feedstream. It is most desirable that the complex product mixture referred to as alkylate contains predominantly trimethylpentanes, since these are high-octane components which add considerable value to motor fuel, yet the chemistry of alkylation affords a dazzling variety of products resulting from only a few basic chemical reactions characteristic of the carbonium ion which plays a central role in the alkylation process. Thus, chain transfer (intermolecular hydride transfer and alkyl shifts), oligomerization and disproportionation serve to place into the alkylate as byproduct materials of from 5–12 +carbon atoms from a feed containing only C4 olefins and alkanes.

The alkylation of olefins is catalyzed by strong acids generally. Although such alkylation has been the focus of intense and continuing scrutiny for several decades, the requirements of optimum selectivity while achieving high conversion have heretofore narrowed, for all practical purposes, the commercial choice of catalyst to sulfuric acid and liquid hydrogen fluoride. While processes based on each of these acids have gained commercial acceptance those based on HF have been favored at least in part because of the relative ease of HF regeneration. A brief but valuable overview of HF-catalyzed alkylation is presented by B. R. Shah in "Handbook of Petroleum Refining Processes", R. A. Meyers, editor, McGraw-Hill Book Company, 1986, pp 1-3 through 1-28.

In a rather over-simplified description, the HF-catalyzed alkylation process is carried out as follows. Olefinic and isobutane feedstocks are combined and mixed with HF in an alkylation reaction zone. The reactor effluent is separated into the desired alkylate, acid, and light gases which are predominantly unreacted isobutane. The HF is either recycled to the reactor directly or regenerated, in whole or in part, prior to its being recycled to the reactor. Unreacted isobutane also is recycled to the reactor, and the alkylate is then used in motor fuel blending.

Recently HF (hydrofluoric acid) has come under environmental pressure. Hydrofluoric acid is classified as an Acutely Hazardous Material, and in Southern California the Board of the South Coast Air Quality Management District recently required that the use of HF in alkylation be phased out by Jan. 1, 1998. Consequently there is increasing reason to seek substitutes for HF as an alkylation catalyst for alkylate production. It is quite desirable to have a solid acid as an effective catalyst, for this permits development of fixed bed processes, a desirable alternative in the petroleum refining industry.

One of the promising solid catalysts for alkylation of C2–C6 olefins with alkanes in the 4 to 6 carbon range, a process hereafter specifically referred to as motor fuel alkylation, is the reaction product between one or more of the metal halides active as Friedel-Crafts catalysts and a refractory inorganic oxide having surface hydroxyl groups, where the refractory inorganic oxide also contains dispersed thereon a metal having hydrogenation activity for olefins. Such catalysts are reasonably well known in the art, as exemplified by U.S. Pat. No. 2,999,074, and includes, for example, the reaction product of aluminum chloride and alumina containing zerovalent platinum. As is commonly the case, these catalysts deactivate with use, where the deactivation is measured by the percent conversion of olefins, and it is imperative to have means of repeatedly regenerating these catalysts, i.e., to restore their activity, in order to utilize their catalytic effectiveness over long periods of time. It is further desirable that the method of regeneration be minimally disruptive to the motor fuel alkylation process itself. By that is meant that it is most desirable that the catalyst not be subjected to conditions or agents foreign to those of the alkylation process itself. It is still further desirable to minimize the regeneration cycle time relative to the alkylation cycle time. That is, if the complete process cycle time be the sum of the time during which the catalyst is used in alkylation (alkylation cycle time) and the time during which the catalyst is regenerated (regeneration cycle time) one desires that the latter be as short as possible. Of course the ideal regeneration cycle time is zero, but this corresponds to the case where the catalyst does not deactivate which, unfortunately, is contrary to experience.

Recently we developed a simple yet effective method of regenerating a deactivated catalyst of the aforedescribed type which satisfies both of the foregoing criteria; U.S. Pat. No. 5,310,713. More particularly, it was disclosed that after removing liquid hydrocarbons from the deactivated catalyst, treatment of the catalyst with hydrogen at approximately the same pressure as that used during alkylation and at reasonably low temperatures affords virtually complete regeneration, often with increased product quality. Our method is simple, very effective both in restoring activity and affording multiple regenerations, and requires a cycle time which is commercially feasible.

Subsequently, an improved catalyst was developed for alkylation where the catalyst was the reaction product of aluminum chloride and, the bound surface hydroxyl groups of, e.g., alumina containing a zerovalent metal having hydrogen activity and a metal cation, especially where the metal cation was one of the alkali or alkaline earth metal cations. Since the regeneration of a catalyst is a function of both the catalyst and the catalytic process causing its deactivation, and since regeneration often varies unpredictably for obscure reasons, or no apparent reason at all, we were gratified to find that the improved catalyst referred to above was regenerated by essentially the same process used for its predecessor catalyst.

SUMMARY OF THE INVENTION

The purpose of our invention is to repeatedly restore the activity of catalysts of metal halides reacted with surface hydroxyl groups of refractory inorganic oxides and which also contain small amounts of a metal active in hydrogenation and a metal cation, usually from the alkali or alkaline earth series, where such catalysts have become deactivated in use as a motor fuel liquid phase alkylation catalyst. One embodiment comprises treating the catalyst freed of all liquid phase with hydrogen at a temperature in the range of 10°-300° C. and at a hydrogen partial pressure in the range of 1-150 atmospheres. In a more specific embodiment the refractory inorganic oxide is alumina. In another specific embodiment the metal halide is aluminum chloride. In a still more specific embodiment the metal halide is aluminum chloride, the refractory inorganic oxide is alumina, the metal having hydrogenation activity is platinum, and the metal cation is potassium. In another embodiment the catalyst is treated with hydrogen at the aforementioned temperature and pressure and in the presence of liquid isobutane and a chloride source. Other embodiments will be apparent from the description which follows.

DESCRIPTION OF THE INVENTION

Although the group of catalysts which may be characterized as the reaction products of a Friedel-Crafts active metal halide and surface hydroxyl groups of inorganic oxides and which additionally contains both a zerovalent metal having hydrogenation activity and a metal cation, largely taken from the alkali metal or alkaline earth metal series, shows promise in the liquid phase alkylation of alkenes with alkanes to produce alkylates valuable as a component of motor fuel, such catalysts deactivate quickly. Therefore there is a need to develop a method of regenerating the catalyst, preferably by procedures which are relatively simple, which are inexpensive, and which are effective in restoring catalytic activity over many multiple regeneration cycles. This application describes such a method, which is to free the catalyst of the liquid phase reaction mixture and then treat the catalysts with hydrogen at temperatures of at least 10° C. up to about 300° C. and at a hydrogen partial pressure at least about 1 to about 150 atmospheres. Treatment of the catalyst with hydrogen may be effected with either liquid-free catalysts or in the presence of a liquid organic material and a chloride source.

The analogs of our catalyst without the metal cations of our invention are well known in the art (see U.S. Pat. No. 2,999,074; cf. 3,318,820) and the extensive descriptions of their preparations are applicable to our catalyst with the exception of impregnation with a monovalent cation or alkaline earth metal cation. Thus, much of the prior art description is applicable to our catalysts and makes a detailed description of their preparation unnecessary. The following description then will suffice merely to afford the reader an understanding of our invention.

The refractory inorganic oxides suitable for use in this invention have a surface area of at least about 35 $m^2/g$, preferably greater than about 50 $m^2/g$, and more desirably greater than 100 $m^2/g$. There appears to be some advantage to working with materials having as high a surface area as possible, although exceptions are known which preclude making this a general statement. Suitable refractory inorganic oxides include alumina, titania, zirconia, chromia, silica, boria, silica-alumina, aluminum phosphate, and combinations thereof. Of these alumina is particularly preferred. Any alumina phase may be used so long as it has a surface area of at least 35 $m^2/g$ and has surface hydroxyl groups. xanong the phases which may be used are included gamma-, eta-, and theta-alumina, although the various phases are not necessarily equivalent in their effectiveness as a motor fuel alkylation catalyst. Aluminum phosphate is another favored refractory material.

It is required that the refractory inorganic oxide have bound surface hydroxyl groups, by which is meant not adsorbed water but rather hydroxyl (OH) groups whose oxygen is bound to the metal of the inorganic oxide. These latter hydroxyl groups sometimes have been referred to as chemically combined hydroxyl. Since the presence of adsorbed water is generally detrimental to the preparation of the catalysts of our invention, the refractory inorganic oxides are first treated to remove surface hydroxyl groups arising from water, most usually by calcination at a temperature which specifically and preferentially removes physically adsorbed water without chemically altering the other hydroxyl groups. For example, calcination temperatures ranging from about 350° C. to about 700° C. are usually satisfactory where the inorganic oxide is alumina.

The catalytic composites of our invention optionally contain a metal having hydrogenation activity. Where a hydrogenation-active metal is present it generally is deposited on the refractory inorganic oxide prior to the reaction of its bound surface hydroxyl groups with metal halides. Although such a procedure has proven both convenient and effective, we do not wish to imply that this is the only sequence which may be used to afford an effective catalyst. Metals which have been found to be particularly effective include nickel, platinum, palladium, ruthenium, rhenium, rhodium, osmium, and iridium, and the Group IB metals of copper, silver, and gold, although platinum, palladium, and silver are by far the most desirable of the metals. The desired metal may be composited with the refractory inorganic oxide in any desired manner, such as by impregnation, coprecipitation, dipping, and so forth, of a suitable salt followed by reduction of the metal to its zerovalent state. Such methods are well known and need not be described here. Hydrogenation-active metal levels may range between about 0.01 up to about 1.0 weight percent for the Group VIII metals, based on the weight of the finished catalyst, and from about 0.1 up to about 5 weight percent for others. The composite of the zerovalent metal, formed by reduction of the oxidized metal, and refractory inorganic oxide is dried and calcined under controlled conditions to remove physically adsorbed water but under sufficiently mild conditions so that the "chemically combined" hydroxyl groups are not eliminated.

The more usual way of introducing a hydrogenation-active metal into the catalytic composites of our invention is by coimpregnation of the refractory inorganic oxide with a salt of the hydrogenation-active metal together with one or more monovalent or alkaline earth metal cations of our invention. But as stated above it is not believed that the particular procedure or sequence used is determinative of success of, or even of substantial significance to, the final catalytic composite.

The next stage in the preparation of our catalytic composites, whether or not a metal with hydrogenation activity has been deposited thereon, is to deposit on the composite one or more monovalent metal or alkaline earth metal cations. Such metals include lithium, sodium, potassium, cesium, rubidium, silver, copper(I), beryllium, magnesium, calcium, strontium, and barium. Among the monovalent metal cations the alkali metal cations are favored. The amount of metal cation which is impregnated on the composite is an amount having a gram atom equivalent from about 0.1 up to about 2 weight percent potassium, which is 0.0026 gram atoms potassium up to 0.051 gram atoms per 100 gram support. We define a "gram atom equivalent" of another metal cation as being a number of gram atoms of the metal divided by its valence per 100 grams support. For example, for magnesium the gram atom equivalent is 0.0013 up to about 0.0255 gram atoms per 100 gram support, which is equal to 0.031 up to about 0.62 weight percent.

Impregnation of the composite by the monovalent metal or alkaline earth metal cation may be done simply by mixing the composite with a suitable aqueous solution of the salt and removing water. The particular monovalent or alkaline earth metal salt used is not especially important so long as it provides sufficient solubility in water. As a practical matter, the halides, nitrates, and acetates may be the most commonly employed salts. Salts prone to precipitation should be avoided in order to avoid non-uniform impregnation, but otherwise there are no serious limitations on the salts which may be used. After evaporation of excess water, materials generally are dried at a temperature between about 100° and 200° C. for 2-4 hours and then calcined at a temperature which specifically and preferentially removes physically adsorbed water without chemically altering the other hydroxyl groups. As mentioned before, temperatures ranging from about 350° C. to about 700° C. usually are satisfactory where the inorganic oxide is alumina.

Subsequent to metal deposition and calcination, the bound surface hydroxyl groups of the refractory inorganic oxide are reacted with a metal halide having Friedel-Crafts activity. Among the metals which may be used are included aluminum, zirconium, tin, tantalum, titanium, gallium, antimony, and boron. Suitable halides are the fluorides, chlorides, and bromides. Representative of such metal halides include aluminum chloride, aluminum bromide, ferric chloride, ferric bromide, zirconium chloride, zirconium bromide, boron trifluoride, titanium tetrachloride, gallium chloride, tin tetrachloride, antimony fluoride, tantalum chloride, tantalum fluoride, and so forth. Of these metal halides the aluminum halides are preferred, especially aluminum chloride. Except for boron trifluoride, the chlorides are generally the preferable halides.

The reaction between the metal halides of this invention and the bound surface hydroxyl groups of the refractory inorganic oxide is readily accomplished by, for example, sublimation or distillation of the metal halide onto the surface of the particles of the metal inorganic oxide composite. The reaction is attended by the elimination of between about 0.5 and 2.0 moles of hydrogen halide per mole of metal halide adsorbed thereon. The reaction temperature will depend upon such variables as the reactivity of the metal halides and its sublimation temperature or boiling point, where the metal halide is reacted in the gas phase, as well as on the nature of the refractory inorganic oxide. For example, using aluminum chloride and alumina as our specific examples reaction readily occurs within the range between about 190° through 600° C.

The amount of metal halide which is reacted with the bound surface hydroxyl groups of the refractory inorganic oxide is generally given in terms of the weight percent of the Friedel-Crafts metal on the composite. This amount will vary with the refractory inorganic oxide used, the relative number of bound surface hydroxyls of the inorganic oxide (which may be related to the particular oxide phase utilized), the specific Friedel-Crafts metal halide employed, as well as the particular procedure used to effect reaction between the Friedel-Crafts type metal halide and the bound surface hydroxyl. As a rough rule of thumb for aluminum chloride on alumina, as an example, the amount of aluminum chloride reacted expressed as weight percent aluminum in the final composite ranges from about 0.1 up to about 2.5%, with the level being a function primarily of the number of bound surface hydroxyl groups on the refractory inorganic oxide.

We have found the following method to be very effective in restoring lost activity to the catalyst and to be effective over many regeneration cycles. It is first necessary to remove all of the liquid reaction mixture from the catalyst, which can be done quite simply by draining all of the liquid phase from the catalyst. After the liquid phase is removed the catalyst is flushed with the alkane and subsequently treated with hydrogen at a partial pressure between about 1 up to about 2,000 psi, generally but optionally in the presence of a halide source, especially a chloride source. The temperature at which the catalyst is treated with hydrogen varies between about 10° and about 300° C. Regeneration time depends inversely with temperature. Consequently, higher temperatures are favored if a shorter regeneration time is desirable, and for this reason temperatures even higher than 300° C. may be used although these are not generally recommended. However, other factors favor low temperatures regeneration. Regeneration at alkylation process conditions is most desirable in order to eliminate the costs of heating and cooling, and to make regeneration operationally simpler and easier. In fact, regeneration is preferably done in the temperature range between about 10° and about 200° C., for which a regeneration time on the order of 6 hours suffices to effect maximum restoration of activity.

In that variant where a liquid phase is present during hydrogen treatment, the liquid phase may be any liquid organic material which simultaneously facilitates transport of hydrogen to the catalyst and transport of organics out of and away from the catalyst. Alkanes as a class are suitable organic liquids, and that variant where the liquid organic phase is the alkane used in alkylation is a preferred one. Other organic liquids which may be used include aromatics such as benzene, toluene, and the xylenes, as well as such materials as decalin and tetralin. To be suitable in the practice of our invention it is preferred that the organic material have a hydrogen solubility of at least about 0.1 percent by weight.

Several halide sources are suitable in the practice of our invention. Perhaps the most convenient source is an organic chloride which, at least formally, is dehydrochlorinated to the alkene being reacted in the alkylation process. Thus, where 2-butene is being alkylated both 1- and 2-chlorobutane are suitable sources. Where isobutylene can be tolerated t-butyl chloride is a suitable chloride source. Another chloride source is hydrogen chloride, although this is not often used because of some undesirable properties such as its corrosivity. The halide source will be used in an amount corresponding to 10–1000 ppm of the halogen; although bromides, and to some extent iodides, may be used in the practice of our invention, chlorides are greatly favored.

EXAMPLES

An extruded alumina support was impregnated with 0.25 weight percent Pt from aqueous chloroplatinic acid to which an additional 2.5 weight percent HCl had been added. After evaporation of the liquid, the catalyst was dried at 150° C. for 2 hours and calcined in air at 500° C. for 2 hours. This material was then impregnated with 1 weight percent K from KCl (aqueous). After drying at 150° C. (2 hrs), the catalyst was calcined in air at 500° C. for 2 hours and then reduced in flowing hydrogen at 500° C. for 2 hours. The catalyst was finished by sublimation of AlCl3 at 260° C.

The pilot plant test was conducted at 30° C., 450 psig, 0.2 olefin WHSC, and 45 isobutane/2-butene feed molar ratio. Results are included in the following table. The regeneration was conducted at 450 psig in flowing hydrogen (3,000 GHSV) for 4 hours at 130° C. The data show the catalyst activity was completely restored. Throughout both runs the conversion of isobutane and butene was essentially stoichiometric to produce a paraffinic product.

TABLE 1

| Hours from Feed Addition | Catalyst Regeneration Olefin Conversion | |
|---|---|---|
| | Before Regeneration | After Regeneration |
| 0.25 | 100 | 100 |
| 0.75 | 100 | 100 |
| 1.25 | 100 | 100 |
| 1.75 | 99.7 | 99.8 |
| 2.25 | 95.5 | 96.2 |
| 2.75 | 87.3 | 86.9 |

Catalyst also may be regenerated in the presence of an alkane, such as isobutane, in the presence of a halide source such as i-butyl chloride cofed with hydrogen at a concentration of 10–1000 ppm based on chlorine. Similar results to that in the table may be obtained.

What is claimed is:

1. A process of regenerating an alkylation catalyst, said catalyst comprising 1) the reaction product of a first metal halide and the bound surface hydroxyl groups of a refractory inorganic oxide, 2) a zerovalent second metal, and 3) a third metal cation, where said first metal halide is a fluoride, chloride, or bromide and the first metal is selected from the group consisting of aluminum, zirconium, tin, tantalum, titanium, gallium, antimony, phosphorus, and boron and any combination thereof, where said second zerovalent metal is selected from the group consisting of platinum, palladium, nickel, ruthenium, rhodium, osmium, iridium, rhenium, silver, copper, and any combination thereof, and where said third metal cation is selected from the group consisting of monovalent metal cations selected from the group consisting of alkali metal, silver, and Cu(I) cations in an amount from 0.0026 up to about 0.051 gram atoms per 100 grams refractory inorganic oxide, alkaline earth metal cations in an amount from about 0.0013 up to about 0.0255 gram atoms per 100 grams of refractory inorganic oxide, and any combination thereof, said catalyst having become at least partially deactivated during its catalysis of the liquid phase alkylation of an alkene having from 2 up to 6 carbon atoms with an alkane having from 4 up to about 6 carbon atoms, said process comprising removing all of the liquid phase from the catalyst, treating said catalyst with hydrogen at a partial pressure of from about 1 up to about 2000 psi for a time from about 1 up to about 20 hours at a temperature from about 10 up to about 300° C. and recovering a regenerated catalyst having substantially increased activity.

2. The process of claim 1 where the first metal is selected from the group consisting of aluminum, zirconium, titanium, gallium, boron, and any combination thereof.

3. The process of claim 2 where the first metal is aluminum.

4. The process of claim 2 where the first metal is zirconium.

5. The process of claim 2 where the first metal is boron.

6. The process of claim 2 where the first metal is gallium.

7. The process of claim 2 where the first metal is titanium.

8. The process of claim 1 where the second metal is platinum, palladium, rhenium, or any combination thereof.

9. The process of claim 1 where the second metal is nickel.

10. The process of claim 1 where the second metal is silver.

11. The process of claim 1 where the third metal cation is an alkali metal cation.

12. The process of claim 11 where the alkali metal cation is a sodium or potassium cation.

13. The process of claim 1 where the third metal cation is an alkaline earth metal cation.

14. The process of claim 13 where the alkaline earth metal cation is the magnesium or calcium cation.

15. The process of claim 1 where the catalyst is treated with hydrogen at a temperature from about 10° to about 200° C.

16. The process of claim 1 further characterized in that hydrogen treatment is performed with a halide source present at a concentration affording from 10 up to about 1000 ppm halogen.

17. The process of claim 16 where the halide is a chloride.

* * * * *